(12) United States Patent
Kamal et al.

(10) Patent No.: US 7,045,341 B2
(45) Date of Patent: May 16, 2006

(54) **CHEMOENZYMATIC PROCESS FOR STEREOSELECTIVE PREPARATION OF *R* AND *S* ENATIOMERS OF 2-HYDROXY-3-(2-THIENYL) PROPANENITRILE**

(75) Inventors: Ahmed Kamal, Hyderabad (IN); Bhasker Ramesh Khanna Gollapalli, Hyderabad (IN); Ramu Rondla, Hyderabad (IN); Venkateswara Rao Maddamsetty, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 474 days.

(21) Appl. No.: 10/393,406

(22) Filed: Mar. 20, 2003

(65) Prior Publication Data

US 2004/0185540 A1    Sep. 23, 2004

(51) Int. Cl.
*C12P 41/00* (2006.01)

(52) U.S. Cl. .................................................... 435/280
(58) Field of Classification Search .................. None
See application file for complete search history.

(56) References Cited

FOREIGN PATENT DOCUMENTS

| WO | 02/057475 | | 7/2002 |
|---|---|---|---|
| WO | 2004/013123 | * | 2/2004 |

* cited by examiner

Primary Examiner—Sandra E. Saucier
(74) Attorney, Agent, or Firm—Ladas & Parry LLP

(57) ABSTRACT

A chemoenzymatic process for the stereoselective preparation of both the (R) and (S) enantiomers of 3-hydroxy-3-(2-thienyl) propanenitrile has been developed. These optically pure key intermediates were prepared by enzymatic resolution of (±)3-hydroxy-3-(2-thienyl) propanenitrile both by transesterification and by hydrolysis reaction which were then transformed to both enantiomers of duloxetine.

12 Claims, No Drawings

CHEMOENZYMATIC PROCESS FOR STEREOSELECTIVE PREPARATION OF R AND S ENATIOMERS OF 2-HYDROXY-3-(2-THIENYL) PROPANENITRILE

FIELD OF THE INVENTION

The present invention relates to a chemoenzymatic process for stereoselective preparation of both R and S enantiomers of 3-hydroxy-3-(2-thienyl) propanenitrile (1).

This invention particularly relates to a chemoenzymatic process for the stereoselective preparation of both the enantiomers of 3-hydroxy-3-(2-thienyl) propanenitrile (2) a key intermediate for the synthesis of antipsychic drug duloxetine.

BACKGROUND OF THE INVENTION

Duloxetine and related class of compounds like fluoxetine, tomoxetine etc., are important for treating psychiatric disorders. Fluoxetine is a selective inhibitor of serotonin in serotonergic neurons, tomoxetine and nisoxetine are selective inhibitors of norepinephrine in noradrenergic neurons while duloxetine is a dual inhibitor of serotonin and norepinephrine reuptake and thus have a better pharmacological profile as an antidepressant drug (EP 273658, 1988; Chem. Abstr., 1988, 109, 170224n; Life Sci 1988, 43, 2049).

Serotonin and norepinephrine neuro transmitters are intimately involved in a number of physiological and behavioral processes, suggesting that duloxetine (ability to produce robust increase of extra cellular serotonin and norepinephrine levels) is not only a highly efficient antidepressant agent for treating psychiatric disorders but also can be used for treating other symptoms like alcoholism, urinary incontinence, fatigue, stroke, intestinal cystitis, obsessive compulsive disorder, panic disorder, hyperactivity disorder,[11] sleep disorder, sexual dysfunction etc.

Duloxetine having one chiral center can exist in two isomeric forms. In view of the different pharmacological activities displayed by individual enantiomers, differences in metabolic behaviour and importance to provide enantiomerically pure forms as drugs, the preparation of this drug in enantiomerically pure form is highly desirable.

Duloxetine has the basic structural skeleton of 3-aminopropanol and retrosynthetic synthetic strategy reveals that enantiomerically pure 3-hydroxy-3-(2-thienyl) propanenitrile (β-hydroxy nitrile) (1) should be an excellent chiral building block for the synthesis of the target molecule. In the literature, there are only few reports for the synthesis of duloxetine in optically pure form, one by employing complexed-LAH for asymmetric reduction of the Mannich base (Tetrahedron Lett. 1990, 31, 7101) and other by lipase mediated resolution of 3-chloro-1-(2-thienyl)-1-propanol (Chirality 2000, 12, 26).

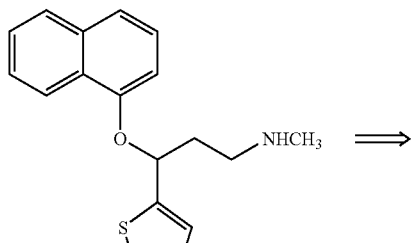

Duloxetine

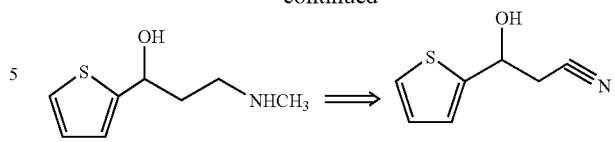

OBJECTS OF THE INVENTION

The main object of the invention is to provide a chemoenzymatic process for the stereoselective preparation of both the enantiomers of 3-hydroxy-3-(2-thienyl) propanenitrile (1) which are optically pure intermediates for the synthesis of both enantiomers of duloxetine in high enantiomeric excess.

In the drawings accompanying this specification represents enzymatic resolution of 3-hydroxy-3-(2-thienyl) propanenitrile via lipase mediated transesterification of 3-hydroxy-3-(2-theinyl) propanenitrile (1) and lipase mediated hydrolysis of 3-acetyloxy-3-(2-thienyl) propanenitrile (2) to afford optically pure hydroxy nitrile and its corresponding acetate.

SUMMARY OF THE INVENTION

Accordingly the present invention provides a chemoenzymatic process for the stereoselective preparation of both R and S enantiomers of 3-hydroxy-3-(2-thienyl) propanenitrile (1), which comprises (i) reacting the cyanohydrin (1) with an acetylating agent in the presence of lipase and then separating the (R)-acetate and (S)-alcohol obtained ii) enzymatically hydrolysing 3-acetyloxy-3-(2-thienyl)propanenitrile (2) in a phosphate buffer solution to provide (S)-acetate and (R)-alcohol.

In one embodiment of the invention, recycling is not required for the products obtained by kinetic resolution since the enantiomeric excess is >99%.

In another embodiment of the invention the acetylating agent is selected from the group consisting of vinyl acetate or isopropenyl acetate.

In yet another embodiment of the invention, the acetylation of the cyanohydrin is done in the presence of a lipase in a solvent.

In a further embodiment of the invention, the solvent is selected from the group consisting of diisopropyl ether; toluene, hexane, dioxane, chloroform, t-butylmethyl ether, diethyl ether, tetrahydrofuran, acetonitrile and acetone.

In yet another embodiment of the invention, the lipase used is selected from the group consisting of Pseudomonas cepacia lipase immobilized on modified ceramic particles (PS-C), Pseudomonas cepacia lipase immobilized on diatomite (PS-D), Psedomonas cepacia (PS), Porcine pancreas lipase (PPL), Candida cylindracea lipase (CCL), Candida rugosa lipase (CRL) and lipase immobilized from Mucor miehei (Lipozyme).

DETAIL DESCRIPTION OF THE INVENTION

The present invention provides an enzymatic process for the stereoselective preparation of both the enantiomers of 3-hydroxy-3-(2-thienyl) propanenitrile (1), a key intermediate for the synthesis of both enantiomers of duloxetine which comprises of reacting the cyanohydrin with acetylating agent and hydrolysis of acetyloxy nitrile in the presence of lipase followed by separation of acetate and alcohol obtained employing column chromatography. The 3-hydroxy-3-(2-thienyl) propanenitrile (1) was selectively acetylated with vinyl acetate, isopropenyl acetate in the presence of lipases while 3-acetyloxy-3-(2-thienyl) propanenitrile (2) was selectively hydrolyzed in phosphate buffer in the presence of the lipases.

The alcohol and the ester formed in the kinetic resolution were separated by column chromatography. The enantiomeric purities of the compounds were determined by HPLC employing a chiral column (OJ-H). Absolute configurations were preliminarily presumed to be R for acetate and S for alcohol (in the transesterification reaction) by the empirical rule for the enantiopreference of the lipase and then later confirmed from the optical rotation values of their corresponding aminoalcohols (*Chirality* 2000, 12, 26).

The process of the present invention is illustrated below:

1. Racemic 3-hydroxy-3-(2-thienyl)propanenitrile (1) was acetylated enzymatically employing different acetylating agents and various lipases in different solvents
2. Acetylating agents such as vinyl acetate and isopropenyl acetate were used for acetylation.
3. Different lipases like *Pseudomonas cepacia* lipase immobilized on modified ceramic particals (PS-C), *Pseudomonas cepacia* lipase immobilized on diatomite (PS-D), *Psedomonas cepacia* (PS), porcine pancreas lipase (PPL), *Candida cylindracea lipase* (CCL), *Candida rugosa* lipase (CRL), lipase immobilized from *Mucor miehei* (Lipozyme) were screened for the enzymatic transesterification process.
4. Various solvents like diisopropyl ether, toluene, hexane, dioxane, chloroform, t-butylmethyl ether, diethyl ether, tetrahydrofuran, acetonitrile and acetone were employed.
5. Racemic 3-acetyloxy-3-(2-thienyl) propanenitrile (2) was prepared by reaction of the hydroxy nitrile with acetic anhydride in the presence of pyridine.
6. Racemic 3-acetyloxy-3-(2-thienyl) propanenitrile (2) was hydrolyzed enzymatically employing various lipases in phosphate buffer solution.
7. In the presence of lipases (R)-3-hydroxy-3-(2-thienyl) propanenitrile was selectively acetylated, and (R)-3-acetyloxy-3-(2-thienyl)propanenitrile was selectively hydrolyzed and the thus obtained acetates and alcohols were separated by column chromatography.
8. The enantiomeric excess was determined by HPLC employing chiral column.

The reaction mechanism is given below:

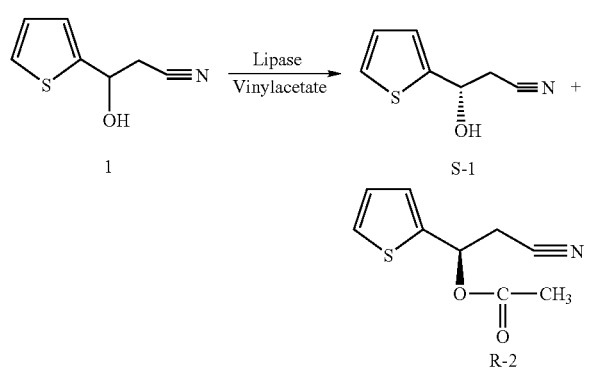

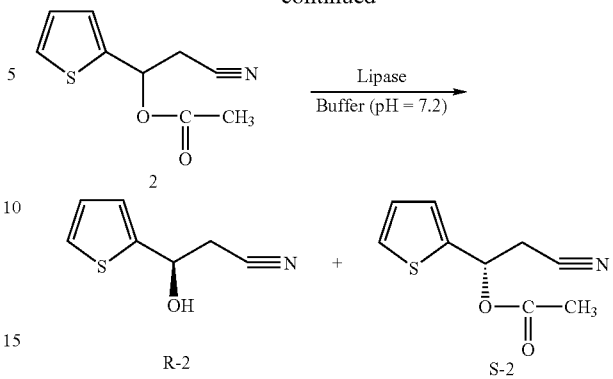

The following examples are given by way of illustration and they should not be construed to limit the scope of the present invention.

EXAMPLE 1

Enzymatic Transesterification of 3-hydroxy-3-(2-thienyl) propanenitrile (1): To a solution of 3-hydroxy-3-(2-thienyl) propanenitrile (1) (5 mmol) dissolved in diisopropyl ether (100 mL), *Pseudomonas cepacia* lipase immobilized on diatomite (PS-D) (500 mg) and vinyl acetate (25 mmol) were added successively and incubated at 25° C. in an orbital shaker. After 50% completion of the reaction (14 h) as indicated by HPLC, the reaction mixture was filtered and solvent was evaporated under reduced pressure. The residue was subjected to column chromatography to separate the acetate formed and the unreacted alcohol. The optical purity of these compounds were determined by HPLC. (S)-3-hydroxy-3-(2-thienyl) propanenitrile (S-1) 42% yield, ee>99%; $[\alpha]^{30}_D = -33.5$ (c 1, CHCl$_3$); IR (Neat) 3475, 3075, 2878, 2251, 1105, 698 cm$^{-1}$; $^1$H NMR (200 MHz, CDCl$_3$) δ 2.82 (dd, 2H, J=3.0 Hz, J=6.6 Hz), 3.0 (s, 1H) 5.25 (t, 1H, J=5.5 Hz), 6.98 (t, 1H, J=4.9 Hz), 7.05 (d, 1H, J=3.7 Hz), 7.28 (d, 1H, J=4.9 Hz); $^{13}$C NMR (75 MHz) δ 28.1, 66.0, 117.0, 124.6, 125.6, 127.0, 144.4; Mass (EI) 153 127, 113, 85.

(R)-3-acetyloxy-3-(2-thienyl) propanenitrile (R-2) 43% yield, ee>99%, $[\alpha]^{30}_D = +83.6$ (c 1, CHCl$_3$); IR (Neat) 3114, 2910, 2800, 2243, 1734, 1216 cm$^{-1}$; $^1$H NMR (200 MHz, CDCl$_3$) δ 2.10 (s, 3H), 2.94 (d, 2H, J=6.7 Hz), 6.20 (t, 1H, J=6.7 Hz), 6.97 (t, 1H, J=3.8 Hz), 7.1 (d, 1H, 3.0 Hz), 7.3 (d, 1H, J=5.9 Hz); Mass (EI) 195, 154, 137, 114, 85, 43.

EXAMPLE 2

Hydrolysis of 3-acetyloxy-3-(2-thienyl)propanenitrile (2): To a solution of 3-acetyloxy -3-(2-thienyl)propanenitrile (5 mmol) in 3 mL of acetone was added phosphate buffer pH=7.2 and *Pseudomonas cepacia* lipase immobilized on diatomite (PS-D) (500 mg) and incubated at 25° C. in an orbital shaker. After 50% completion of the reaction (16 h) as indicated by HPLC, the reaction mixture was filtered and the filtrate was extracted with ethyl acetate and organic solvent was evaporated under reduced pressure to leave a residue. The residue was subjected to column chromatography to separate the unreacted acetate and the alcohol formed. The optical purity of these compounds were determined by HPLC.

Yield of (R)-3-hydroxy-3-(2-thienyl)propanenitrile (R-1) 42%, ee >99%; $[\alpha]^{30}_D = +32.0$ (c 1, CHCl$_3$);

Yield of (S)-3-acetyloxy-3-(2-thienyl) propanenitrile (S-2) 43%, ee >99%, $[\alpha]^{30}_D = -82.1$ (c 1, $CHCl_3$).

EXAMPLE 3

Chiral HPLC Analysis: HPLC analysis was performed on an instrument that consisted of a Shiimadzu LC-6A system controller, SPD-6A fixed wavelength UV monitor as detector, FCV-100B fraction collector and chromatopac C-R4A data processor as a recording integrator. Analyses were performed by employing chiral column (Chiralcel OJ-H, Daicel) with hexane: isopropanol (85:15) as the mobile phase at a flow rate of 0.75 mL/min and monitored at UV 254 nm. Racemic acetate was prepared by treating its corresponding hydroxy nitrile with acetic anhydride in the presence of pyridine as an authentic sample for comparision on HPLC.

The main advantages of the present invention are:

Vicinal cyanohydrins or 1,2-cyanohyrins are important and versatile compounds in organic synthesis as these hydroxy nitriles in optically pure form provides a number of opportunities for synthetic manipulations leading to a wide range of chiral synthons like amino alcohols, hydroxy amides, hydroxy esters, hydroxy acids etc., by employing simple methods. Moreover, thiophene can serve as a masked alkyl chain or masked acid group making it more useful intermediate for synthesis chirally pure compounds of biological importance.

In this process chiral 1,2-cyanohydrin has been obtained by lipase mediated resolution of the racemate by transesterification as well as hydrolysis in high enantiomeric excess.

We claim:

1. A chemoenzymatic process for the stereoselective preparation of 3-hydroxy-3-(2-thienyl)propanenitrile which comprises stereoselectively reacting 3-hydroxy-3-(2-thienyl)propanenitrile with an acetylating agent using lipase to produce (R)-3-acetoxy-3-(2-thienyl)propanenitrile and (S)-3-hydroxy-3-(2-thienyl)propanenitrile and separating the (R)-3-acetoxy-3-(2-thienyl)propanenitrile and (S)-3-hydroxy-3-(2-thienyl)propanenitrile obtained.

2. The process of claim 1, wherein the enantiomeric excess is greater than 99%.

3. The process of claim 1, wherein the acetylating agent is vinyl acetate or isopropenyl acetate.

4. The process of claim 1, wherein the reacting is effected in an organic solvent.

5. The process of claim 4, wherein the solvent is selected from the group consisting of diisopropyl ether, toluene, hexane, dioxane, chloroform, t-butylmethyl ether, diethyl ether, tetrahydrofuran, acetonitrile and acetone.

6. The process of claim 1, wherein the lipase is selected from the group consisting of lipase derived from *Pseudomonas cepacia* which is immobilized on modified ceramic particles or on diatomite, porcine pancreas lipase, *Candida cylindracea* lipase, *Candida rugosa* lipase or lipase from *Mucor miehei* which is immobilized.

7. A chemoenzymatic process for the stereoselective preparation of 3-hydroxy-3-(2-thienyl)propanenitrile which comprises stereoselectively hydrolyzing 3-acetoxy-3-(2-thienyl)propanenitrile with a lipase in a phosphate buffer solution to produce (S)-3-acetoxy-3-(2-thienyl)propanenitrile and (R)-3-hydroxy-3-(2-thienyl)propanenitrile and separating the (S)-3-acetoxy-3-(2-thienyl)propanenitrile and (R)-3-hydroxy-3-(2-thienyl)propanenitrile obtained.

8. The process of claim 7, wherein the enantiomeric excess is greater than 99%.

9. The process of claim 7, wherein the acetylating agent is vinyl acetate or isopropenyl acetate.

10. The process of claim 7, wherein the reacting is effected in an organic solvent.

11. The process of claim 10, wherein the solvent is selected from the group consisting of diisopropyl ether, toluene, hexane, dioxane, chloroform, t-butylmethyl ether, diethyl ether, tetrahydrofuran, acetonitrile and acetone.

12. The process of claim 7, wherein the lipase is selected from the group consisting of lipase derived from *Pseudomonas cepacia* which is immobilized on modified ceramic particles or on diatomite, porcine pancreas lipase, *Candida cylindracea* lipase, *Candida rugosa* lipase or lipase from *Mucor miehei* which is immobilized.

* * * * *